US010828404B2

(12) United States Patent
Vess et al.

(10) Patent No.: US 10,828,404 B2
(45) Date of Patent: Nov. 10, 2020

(54) SYSTEM FOR PROVIDING CONTINUAL DRAINAGE IN NEGATIVE PRESSURE WOUND THERAPY

(71) Applicant: Smith & Nephew, Inc., Memphis, TN (US)

(72) Inventors: Mark A. Vess, Hanson, MA (US); Chirag B. Shah, North Attleboro, MA (US); Richard M. Braga, North Easton, MA (US); David R. Swisher, St. Charles, MO (US)

(73) Assignee: Smith & Nephew, Inc., Memphis, TN (US)

( * ) Notice: Subject to any disclaimer, the term of this patent is extended or adjusted under 35 U.S.C. 154(b) by 390 days.

(21) Appl. No.: 15/872,810

(22) Filed: Jan. 16, 2018

(65) Prior Publication Data
US 2018/0140757 A1 May 24, 2018

Related U.S. Application Data

(60) Continuation of application No. 14/333,026, filed on Jul. 16, 2014, now Pat. No. 9,889,241, which is a
(Continued)

(51) Int. Cl.
*A61M 1/00* (2006.01)
*A61F 13/02* (2006.01)
*A61F 13/00* (2006.01)

(52) U.S. Cl.
CPC ......... *A61M 1/0092* (2014.02); *A61F 13/023* (2013.01); *A61M 1/0023* (2013.01);
(Continued)

(58) Field of Classification Search
CPC .............. A61F 2013/00174–00178; A61F 2013/00217–00234; A61F 13/02–0243;
(Continued)

(56) References Cited

U.S. PATENT DOCUMENTS 3,026,874 A 3/1962 Stevens
3,367,332 A 2/1968 Groves
(Continued)

FOREIGN PATENT DOCUMENTS

AU 674837 B2 1/1997
DE 41 11 122 A1 4/1993
(Continued)

OTHER PUBLICATIONS

US 6,216,701 B1, 04/2001, Heaton et al. (withdrawn)
(Continued)

*Primary Examiner* — Susan S Su
(74) *Attorney, Agent, or Firm* — Knobbe, Martens, Olson & Bear, LLP

(57) ABSTRACT

A system for subatmospheric pressure therapy in connection with healing a wound is provided. The system includes a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system further includes an exudate conduit in fluid communication with the wound dressing and the collection canister for collecting exudate removed from the reservoir and deposited in the collection canister under influence of the vacuum source and a vent conduit in fluid communication with the collection canister and the wound dressing for introducing air into the reservoir to facilitate flow of exudate through the exudate conduit.

17 Claims, 11 Drawing Sheets

Related U.S. Application Data continuation of application No. 13/571,548, filed on Aug. 10, 2012, now Pat. No. 8,784,392, which is a division of application No. 12/475,954, filed on Jun. 1, 2009, now Pat. No. 8,298,200.

(52) U.S. Cl.
CPC ........ *A61M 1/0084* (2013.01); *A61M 1/0086* (2014.02); *A61F 2013/00089* (2013.01); *A61F 2013/00174* (2013.01); *A61M 2205/7518* (2013.01); *A61M 2205/7536* (2013.01)

(58) Field of Classification Search
CPC .......... A61F 2013/0017; A61M 1/0023–0064; A61M 1/0088–0092; A61M 27/00–002
See application file for complete search history.

(56) References Cited

U.S. PATENT DOCUMENTS

| | | |
|---|---|---|
| 3,486,504 A | 12/1969 | Austin, Jr. |
| 3,568,675 A | 3/1971 | Harvey |
| 3,572,340 A | 3/1971 | Lloyd et al. |
| 3,712,298 A | 1/1973 | Snowdon et al. |
| 3,809,086 A | 5/1974 | Schachet et al. |
| 3,874,387 A | 4/1975 | Barbieri |
| 3,972,328 A | 8/1976 | Chen |
| 3,980,166 A | 9/1976 | DeFeudis |
| 4,063,556 A | 12/1977 | Thomas et al. |
| 4,080,970 A | 3/1978 | Miller |
| 4,112,947 A | 9/1978 | Nehring |
| 4,112,949 A | 9/1978 | Rosenthal et al. |
| 4,136,696 A | 1/1979 | Nehring |
| 4,202,331 A | 5/1980 | Yale |
| 4,224,945 A | 9/1980 | Cohen |
| 4,228,798 A | 10/1980 | Deaton |
| 4,266,545 A | 5/1981 | Moss |
| 4,280,680 A | 7/1981 | Payne |
| 4,382,441 A | 5/1983 | Svedman |
| 4,510,802 A | 4/1985 | Peters |
| 4,524,064 A | 6/1985 | Nambu |
| 4,538,645 A | 9/1985 | Perach |
| 4,605,399 A | 8/1986 | Weston et al. |
| 4,655,754 A | 4/1987 | Richmond et al. |
| 4,700,479 A | 10/1987 | Saito et al. |
| 4,710,165 A | 12/1987 | McNeil et al. |
| 4,738,257 A | 4/1988 | Meyer et al. |
| 4,743,232 A | 5/1988 | Kruger |
| 4,807,625 A | 2/1989 | Singleton |
| 4,870,975 A | 10/1989 | Cronk et al. |
| 4,874,363 A | 10/1989 | Abell |
| 4,921,492 A | 5/1990 | Schultz et al. |
| 4,969,880 A | 11/1990 | Zamierowski |
| 4,990,137 A | 2/1991 | Graham |
| 4,995,863 A | 2/1991 | Nichols et al. |
| 4,997,438 A | 3/1991 | Nipper |
| 5,071,409 A | 12/1991 | Rosenberg |
| 5,100,395 A | 3/1992 | Rosenberg |
| 5,100,396 A | 3/1992 | Zamierowski |
| 5,106,629 A | 4/1992 | Cartmell et al. |
| 5,135,485 A | 8/1992 | Cohen et al. |
| 5,141,503 A | 8/1992 | Sewell, Jr. |
| 5,149,331 A | 9/1992 | Ferdman et al. |
| 5,152,757 A | 10/1992 | Eriksson |
| 5,160,322 A | 11/1992 | Scheremet et al. |
| 5,176,663 A | 1/1993 | Svedman et al. |
| 5,178,157 A | 1/1993 | Fanlo |
| 5,180,375 A | 1/1993 | Feibus |
| 5,195,977 A | 3/1993 | Pollitt |
| 5,238,732 A | 8/1993 | Krishnan |
| 5,261,893 A | 11/1993 | Zamierowski |
| 5,263,922 A | 11/1993 | Sova et al. |
| D364,679 S | 11/1995 | Heaton et al. |
| 5,484,427 A | 1/1996 | Gibbons |
| 5,527,293 A | 6/1996 | Zamierowski |
| 5,536,233 A | 7/1996 | Khouri |
| 5,549,584 A | 8/1996 | Gross |
| 5,588,958 A | 12/1996 | Cunningham et al. |
| 5,599,289 A | 2/1997 | Castellana |
| 5,624,374 A | 4/1997 | Von Iderstein |
| 5,636,643 A | 6/1997 | Argenta et al. |
| 5,645,081 A | 7/1997 | Argenta et al. |
| 5,678,564 A | 10/1997 | Lawrence et al. |
| 5,701,917 A | 12/1997 | Khouri |
| 5,733,305 A | 3/1998 | Fleischmann |
| 5,735,833 A | 4/1998 | Olson |
| 5,759,570 A | 6/1998 | Arnold |
| 5,779,657 A | 7/1998 | Daneshvar |
| 5,795,584 A | 8/1998 | Totakura et al. |
| 5,840,049 A | 11/1998 | Tumey et al. |
| 5,911,222 A | 6/1999 | Lawrence et al. |
| 5,944,703 A | 8/1999 | Dixon et al. |
| 5,960,837 A | 10/1999 | Cude |
| 6,010,524 A | 1/2000 | Fleischmann |
| 6,071,267 A | 6/2000 | Zamierowski |
| 6,117,111 A | 9/2000 | Fleischmann |
| 6,135,116 A | 10/2000 | Vogel et al. |
| D434,150 S | 11/2000 | Tumey et al. |
| 6,142,982 A | 11/2000 | Hunt et al. |
| 6,174,306 B1 | 1/2001 | Fleischmann |
| 6,203,563 B1 | 3/2001 | Fernandez |
| 6,261,276 B1 | 7/2001 | Reitsma |
| 6,325,788 B1 | 12/2001 | McKay |
| 6,345,623 B1 | 2/2002 | Heaton et al. |
| 6,348,423 B1 | 2/2002 | Griffiths et al. |
| 6,395,955 B1 | 5/2002 | Roe et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,458,109 B1 | 10/2002 | Henley et al. |
| 6,488,643 B1 | 12/2002 | Tumey et al. |
| 6,500,112 B1 | 12/2002 | Khouri |
| D469,175 S | 1/2003 | Hall et al. |
| D469,176 S | 1/2003 | Hall et al. |
| 6,520,982 B1 | 2/2003 | Boynton et al. |
| 6,547,255 B1 | 4/2003 | Donaway et al. |
| 6,553,998 B2 | 4/2003 | Heaton et al. |
| D475,134 S | 5/2003 | Randolph |
| 6,557,704 B1 | 5/2003 | Randolph |
| D478,659 S | 8/2003 | Hall et al. |
| 6,607,495 B1 | 8/2003 | Skalak et al. |
| 6,626,891 B2 | 9/2003 | Ohmstede |
| 6,648,862 B2 | 11/2003 | Watson |
| 6,682,506 B1 | 1/2004 | Navarro |
| 6,685,681 B2 | 2/2004 | Lockwood et al. |
| 6,695,823 B1 | 2/2004 | Lina et al. |
| 6,695,824 B2 | 2/2004 | Howard et al. |
| D488,558 S | 4/2004 | Hall |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B2 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,960,190 B2 | 11/2005 | Stinson |
| 6,979,324 B2 | 12/2005 | Bybordi et al. |
| D515,701 S | 2/2006 | Horhota et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,037,254 B2 | 5/2006 | O'Connor et al. |
| 7,052,167 B2 | 5/2006 | Vanderschuit |
| 7,070,584 B2 | 7/2006 | Johnson et al. |

(56) References Cited

U.S. PATENT DOCUMENTS

| | | | |
|---|---|---|---|
| 7,077,832 B2 | 7/2006 | Fleischmann |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hanningan et al. |
| 7,169,151 B1 | 1/2007 | Lytinas |
| 7,182,758 B2 | 2/2007 | McCraw |
| 7,195,624 B2 | 3/2007 | Lockwood et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,438,705 B2 | 10/2008 | Karpowicz et al. |
| 7,485,112 B2 | 2/2009 | Karpowicz et al. |
| 7,503,910 B2 | 3/2009 | Adahan |
| 7,531,711 B2 | 5/2009 | Sigurjonsson et al. |
| 7,534,927 B2 | 5/2009 | Lockwood et al. |
| 7,553,306 B1 | 6/2009 | Hunt et al. |
| 7,569,742 B2 | 8/2009 | Haggstrom et al. |
| 7,612,247 B2 | 11/2009 | Oyaski |
| 7,615,036 B2 | 11/2009 | Joshi et al. |
| 7,625,362 B2 | 12/2009 | Boehringer et al. |
| 7,645,269 B2 | 1/2010 | Zamierowski |
| 7,651,484 B2 | 1/2010 | Heaton et al. |
| 7,670,323 B2 | 3/2010 | Hunt et al. |
| 7,678,102 B1 | 3/2010 | Heaton |
| 7,686,785 B2 | 3/2010 | Boehringer et al. |
| 7,699,823 B2 | 4/2010 | Haggstrom et al. |
| 7,700,819 B2 | 4/2010 | Ambrosio et al. |
| 7,722,582 B2 | 5/2010 | Lina et al. |
| 7,723,560 B2 | 5/2010 | Lockwood et al. |
| 7,731,702 B2 | 6/2010 | Bybordi et al. |
| 7,775,998 B2 | 8/2010 | Riesinger |
| 7,776,028 B2 | 8/2010 | Miller et al. |
| 7,794,438 B2 | 9/2010 | Henley et al. |
| 7,811,269 B2 | 10/2010 | Boynton et al. |
| 7,837,673 B2 | 11/2010 | Vogel |
| 7,846,141 B2 | 12/2010 | Weston |
| 7,857,806 B2 | 12/2010 | Karpowicz et al. |
| 7,862,718 B2 | 1/2011 | Doyen et al. |
| 7,880,050 B2 | 2/2011 | Robinson et al. |
| 7,896,856 B2 | 3/2011 | Petrosenko et al. |
| 7,909,805 B2 | 3/2011 | Weston |
| 7,910,791 B2 | 3/2011 | Coffey |
| 7,922,703 B2 | 4/2011 | Riesinger |
| 7,927,318 B2 | 4/2011 | Risk, Jr. et al. |
| 7,964,766 B2 | 6/2011 | Blott et al. |
| 7,976,519 B2 | 7/2011 | Bubb et al. |
| 7,981,098 B2 | 7/2011 | Boehringer et al. |
| 7,999,145 B2 | 8/2011 | Kairinos |
| 8,021,347 B2 | 9/2011 | Vitaris et al. |
| 8,034,037 B2 | 10/2011 | Adams et al. |
| 8,062,272 B2 | 11/2011 | Weston |
| 8,083,712 B2 | 12/2011 | Biggie et al. |
| 8,133,211 B2 | 3/2012 | Cavanaugh, II et al. |
| 8,147,468 B2 | 4/2012 | Barta et al. |
| 8,148,595 B2 | 4/2012 | Robinson et al. |
| 8,152,785 B2 | 4/2012 | Vitaris |
| 8,158,844 B2 | 4/2012 | McNeil |
| 8,162,907 B2 | 4/2012 | Heagle |
| 8,168,848 B2 | 5/2012 | Lockwood et al. |
| 8,187,237 B2 | 5/2012 | Seegert |
| 8,188,331 B2 | 5/2012 | Barta et al. |
| 8,202,261 B2 | 6/2012 | Kazala, Jr. et al. |
| 8,235,972 B2 | 8/2012 | Adahan |
| 8,241,261 B2 | 8/2012 | Randolph et al. |
| 8,246,606 B2 | 8/2012 | Stevenson et al. |
| 8,267,908 B2 | 9/2012 | Coulthard |
| 8,298,200 B2 | 10/2012 | Vess et al. |
| 8,308,703 B2 | 11/2012 | Heaton et al. |
| 8,376,972 B2 | 2/2013 | Fleischmann |
| 8,382,731 B2 | 2/2013 | Johannison |
| 8,430,867 B2 | 4/2013 | Robinson et al. |
| 8,506,554 B2 | 8/2013 | Adahan |
| 8,545,466 B2 | 10/2013 | Andresen et al. |
| 8,617,129 B2 | 12/2013 | Hartwell |
| 8,641,691 B2 | 2/2014 | Fink et al. |
| 8,734,410 B2 | 5/2014 | Hall et al. |
| 8,784,392 B2 | 7/2014 | Vess et al. |
| 9,017,302 B2 | 4/2015 | Vitaris et al. |
| 9,033,942 B2 | 5/2015 | Vess |
| 9,227,000 B2 | 1/2016 | Fink et al. |
| 9,302,032 B2 | 4/2016 | Bannister et al. |
| 9,452,245 B2 | 9/2016 | Jaeb et al. |
| 9,474,654 B2 | 10/2016 | Heagle et al. |
| 9,642,950 B2 | 5/2017 | Hartwell |
| 2001/0020145 A1 | 9/2001 | Satterfield |
| 2001/0031943 A1 | 10/2001 | Urie |
| 2001/0043943 A1 | 11/2001 | Coffey |
| 2002/0016577 A1 | 2/2002 | Ohmstede |
| 2002/0108614 A1 | 8/2002 | Schultz |
| 2002/0143286 A1 | 10/2002 | Tumey |
| 2002/0151836 A1 | 10/2002 | Burden |
| 2003/0078532 A1 | 4/2003 | Ruszczak et al. |
| 2003/0093041 A1 | 5/2003 | Risk, Jr. et al. |
| 2003/0181850 A1 | 9/2003 | Diamond et al. |
| 2003/0212357 A1 | 11/2003 | Pace |
| 2003/0212359 A1 | 11/2003 | Butler |
| 2003/0219469 A1 | 11/2003 | Johnson et al. |
| 2004/0039415 A1 | 2/2004 | Zamierowski |
| 2004/0064111 A1 | 4/2004 | Lockwood et al. |
| 2004/0064132 A1 | 4/2004 | Boehringer et al. |
| 2004/0093026 A1 | 5/2004 | Weidenhagen et al. |
| 2004/0113309 A1 | 6/2004 | Thompson, Jr. et al. |
| 2004/0122434 A1 | 6/2004 | Argenta et al. |
| 2004/0167482 A1 | 8/2004 | Watson |
| 2004/0193218 A1 | 9/2004 | Butler |
| 2004/0241213 A1 | 12/2004 | Bray |
| 2004/0249353 A1 | 12/2004 | Risks, Jr. et al. |
| 2004/0260230 A1 | 12/2004 | Randolph |
| 2005/0020955 A1 | 1/2005 | Sanders et al. |
| 2005/0085795 A1 | 4/2005 | Lockwood et al. |
| 2005/0090787 A1 | 4/2005 | Risk, Jr. et al. |
| 2005/0101940 A1 | 5/2005 | Radl et al. |
| 2005/0107756 A1 | 5/2005 | McCraw |
| 2005/0131327 A1 | 6/2005 | Lockwood et al. |
| 2005/0137539 A1 | 6/2005 | Biggie et al. |
| 2005/0147562 A1 | 7/2005 | Hunter et al. |
| 2005/0177190 A1 | 8/2005 | Zamierowski |
| 2005/0182445 A1 | 8/2005 | Zamierowski |
| 2006/0029650 A1 | 2/2006 | Coffey |
| 2006/0039742 A1 | 2/2006 | Cable, Jr. et al. |
| 2006/0100586 A1 | 5/2006 | Karpowicz et al. |
| 2006/0149170 A1 | 7/2006 | Boynton et al. |
| 2007/0005028 A1 | 1/2007 | Risk, Jr. et al. |
| 2007/0014837 A1 | 1/2007 | Johnson et al. |
| 2007/0016152 A1 | 1/2007 | Karpowicz et al. |
| 2007/0021697 A1 | 1/2007 | Ginther et al. |
| 2007/0027414 A1 | 2/2007 | Hoffman et al. |
| 2007/0032754 A1 | 2/2007 | Walsh |
| 2007/0032755 A1 | 2/2007 | Walsh |
| 2007/0032778 A1 | 2/2007 | Heaton et al. |
| 2007/0055209 A1 | 3/2007 | Patel et al. |
| 2007/0078432 A1 | 4/2007 | Halseth et al. |
| 2007/0179460 A1 | 8/2007 | Adahan |
| 2007/0219513 A1 | 9/2007 | Lina et al. |
| 2007/0225663 A1 | 9/2007 | Watt et al. |
| 2007/0233022 A1 | 10/2007 | Henley et al. |

(56) References Cited

U.S. PATENT DOCUMENTS

| | | |
|---|---|---|
| 2008/0011667 A1 | 1/2008 | Ruschke |
| 2008/0071235 A1 | 3/2008 | Locke et al. |
| 2008/0082084 A1 | 4/2008 | Roberts et al. |
| 2008/0103462 A1 | 5/2008 | Wenzel et al. |
| 2008/0132819 A1 | 6/2008 | Radl et al. |
| 2008/0167593 A1 | 7/2008 | Flesichmann |
| 2008/0183233 A1 | 7/2008 | Koch et al. |
| 2008/0200857 A1 | 8/2008 | Lawhorn |
| 2008/0200906 A1 | 8/2008 | Sanders et al. |
| 2008/0208147 A1 | 8/2008 | Argenta et al. |
| 2008/0234641 A1 | 9/2008 | Locke et al. |
| 2008/0306456 A1 | 12/2008 | Riesinger |
| 2009/0131892 A1 | 5/2009 | Karpowicz et al. |
| 2009/0157016 A1 | 6/2009 | Adahan |
| 2009/0293887 A1 | 12/2009 | Wilkes et al. |
| 2009/0299249 A1 | 12/2009 | Wilkes et al. |
| 2009/0299255 A1 | 12/2009 | Kazala, Jr. et al. |
| 2009/0299257 A1 | 12/2009 | Long et al. |
| 2009/0299308 A1 | 12/2009 | Kazala et al. |
| 2009/0299340 A1 | 12/2009 | Kazala et al. |
| 2010/0057025 A1 | 3/2010 | Aicher |
| 2010/0069850 A1 | 3/2010 | Fabo |
| 2010/0137775 A1 | 6/2010 | Hu et al. |
| 2010/0160901 A1 | 6/2010 | Hu et al. |
| 2011/0130712 A1 | 6/2011 | Topaz |
| 2012/0116334 A1 | 5/2012 | Albert et al. |
| 2012/0302976 A1 | 11/2012 | Locke et al. |
| 2013/0226115 A1 | 8/2013 | Robinson et al. |
| 2013/0226152 A1 | 8/2013 | Zolli |
| 2015/0018785 A1 | 1/2015 | Vess |

FOREIGN PATENT DOCUMENTS

| | | |
|---|---|---|
| DE | 43 06 478 | 9/1994 |
| DE | 295 04 378 U1 | 10/1995 |
| EP | 0 358 302 | 3/1990 |
| EP | 0 392 640 B1 | 6/1995 |
| EP | 0 441 418 B1 | 7/1995 |
| EP | 0 751 757 B1 | 1/1997 |
| EP | 0 853 950 | 7/1998 |
| EP | 0 777 504 B1 | 10/1998 |
| EP | 1 088 569 | 4/2001 |
| EP | 1 169 071 A1 | 1/2002 |
| EP | 1 219 311 | 7/2002 |
| EP | 1 487 389 | 12/2004 |
| EP | 0 982 015 B1 | 8/2006 |
| EP | 1 905 465 B1 | 1/2010 |
| EP | 2 319 550 | 5/2011 |
| EP | 1 578 477 B1 | 9/2011 |
| EP | 2 413 858 | 2/2012 |
| EP | 2 529 766 | 12/2012 |
| EP | 2 545 946 | 3/2013 |
| EP | 2 628 500 | 5/2014 |
| EP | 1 339 366 | 6/2014 |
| EP | 2 051 675 | 6/2014 |
| EP | 2 437 802 | 5/2016 |
| FR | 1163907 | 10/1958 |
| GB | 488232 | 7/1938 |
| GB | 1415096 | 11/1975 |
| GB | 1 549 756 | 8/1979 |
| GB | 2195255 A | 4/1988 |
| GB | 2 235 877 A | 3/1991 |
| GB | 2307180 A | 11/1996 |
| GB | 2329127 A | 3/1999 |
| GB | 2336546 A | 10/1999 |
| GB | 2307180 B | 6/2000 |
| GB | 2336546 B | 6/2000 |
| GB | 2344531 A | 6/2000 |
| GB | 2415908 | 1/2006 |
| SU | 1762940 | 1/1989 |
| WO | WO 1980/01139 | 6/1980 |
| WO | WO 1980/02182 | 10/1980 |
| WO | WO 1984/01904 | 5/1984 |
| WO | WO 1989/05133 | 6/1989 |
| WO | WO 1990/11795 | 10/1990 |
| WO | WO 1992/19313 | 11/1992 |
| WO | WO 1993/009727 | 5/1993 |
| WO | WO 1994/20041 | 9/1994 |
| WO | WO 1996/05873 | 2/1996 |
| WO | WO 2000/21586 | 4/2000 |
| WO | WO 2003/005943 | 1/2003 |
| WO | WO 2003/018098 | 3/2003 |
| WO | WO 2003/030966 | 4/2003 |
| WO | WO 2003/045492 | 6/2003 |
| WO | WO 2003/057070 | 7/2003 |
| WO | WO 2003/057071 | 7/2003 |
| WO | WO 2003/057307 | 7/2003 |
| WO | WO 2003/086232 | 10/2003 |
| WO | WO 2003/092620 | 11/2003 |
| WO | WO 2003/101508 | 12/2003 |
| WO | WO 2004/018020 | 3/2004 |
| WO | WO 2005/009488 | 2/2005 |
| WO | WO 2005/016179 | 2/2005 |
| WO | WO 2005/061025 | 7/2005 |
| WO | WO 2006/015599 | 2/2006 |
| WO | WO 2006/105892 | 10/2006 |
| WO | WO 2007/006306 | 1/2007 |
| WO | WO 2007/013064 | 2/2007 |
| WO | WO 2007/016590 | 2/2007 |
| WO | WO 2007/019038 | 2/2007 |
| WO | WO 2007/041642 | 4/2007 |
| WO | WO 2007/085396 | 8/2007 |
| WO | WO 2007/092397 | 8/2007 |
| WO | WO 2007/095180 | 8/2007 |
| WO | WO 2007/106590 | 9/2007 |
| WO | WO 2007/106591 | 9/2007 |
| WO | WO 2008/008032 | 1/2008 |
| WO | WO 2008/012278 | 1/2008 |
| WO | WO 2008/020862 | 2/2008 |
| WO | WO 2008/027449 | 3/2008 |
| WO | WO 2008/043067 | 4/2008 |
| WO | WO 2008/048481 | 4/2008 |
| WO | WO 2008/100440 | 8/2008 |
| WO | WO 2008/100446 | 8/2008 |
| WO | WO 2008/131895 | 11/2008 |
| WO | WO 2008/135997 | 11/2008 |
| WO | WO 2008/141470 | 11/2008 |
| WO | WO 2009/066104 | 5/2009 |
| WO | WO 2009/068665 | 6/2009 |
| WO | WO 2009/086580 | 7/2009 |
| WO | WO 2009/088925 | 7/2009 |
| WO | WO 2009/111655 | 9/2009 |
| WO | WO 2009/137194 | 11/2009 |
| WO | WO 2009/140376 | 11/2009 |
| WO | WO 2009/141820 | 11/2009 |
| WO | WO 2009/145894 | 12/2009 |
| WO | WO 2010/014177 | 2/2010 |
| WO | WO 2010/033769 | 3/2010 |
| WO | WO 2010/042240 | 4/2010 |
| WO | WO 2010/051073 | 5/2010 |
| WO | WO 2010/059730 | 5/2010 |
| WO | WO 2010/078166 | 7/2010 |
| WO | WO 2010/147533 | 12/2010 |
| WO | WO 2011/049562 | 4/2011 |
| WO | WO 2011/100851 | 8/2011 |
| WO | WO 2011/115908 | 9/2011 |
| WO | WO 2012/142002 | 10/2012 |
| WO | WO 2012/166428 | 12/2012 |
| WO | WO 2012/174672 | 12/2012 |
| WO | WO 2013/013938 | 1/2013 |
| WO | WO 2013/016239 | 1/2013 |
| WO | WO 2013/019438 | 2/2013 |
| WO | WO 2013/043972 | 3/2013 |
| WO | WO 2013/123005 | 8/2013 |
| WO | WO 2014/066057 | 5/2014 |
| WO | WO 2014/043238 | 9/2014 |
| WO | WO 2014/158526 | 10/2014 |

OTHER PUBLICATIONS

US 7,186,244 B1, 03/2007, Hunt et al. (withdrawn)
International Search Report and Written Opinion, re PCT Application No. PCT/US2009/046580, dated Jul. 29, 2009.

(56) References Cited

OTHER PUBLICATIONS

International Preliminary Report on Patentability, re PCT Application No. PCT/US2009/046580, dated Dec. 15, 2011.
Annex to the Communication, re the Opposition of European Patent No. EP 2 437 802, dated Oct. 6, 2017, in 13 pages.
Grounds for the Decision, re the Opposition of European U.S. Pat. No. 2 437 802, dated Nov. 2, 2018, in 42 pages.
Written Submission in Response to the Summons to Oral Proceedings, re the Opposition of European Pat. No. 2 437 802, dated May 25, 2018, in 38 pages.
Written Submissions in Preparation to Oral Proceedings, re the Opposition of European Pat. No. 2 437 802, dated Apr. 17, 2018, in 30 pages.
Fleischmann, W. et al., "Vacuum Sealing: Indication, Technique and Results", Emr J Orthop Surg Tramatol (1995) 5:37-40.
Aubrey, D.A., et al., Treatment of the Perineal Wound after Proctectomy by Intermittent Irrigation, Arch. Surg., Oct. 1984, 119, 1141-1144.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Bier, A., Hyperemia as a Therapeutic Agent, Ed. Dr. Gustavus M. Blech, A. Robertson & Co., Chicago 1905.
Arnljots, et al., "Irrigation Treatment in Split-thickness Skin Grafting of Intractable Leg Ulcers," Scand J Plast Reconstr Surg 19: 211-213,1985.
Brochure for the Boehringer Engenex, Aug. 2007, in 33 pages.
Bucalo et al. "Inhibition of Cell Proliferation by Chronic Wound Fluid." Wound Repair and Regeneration. Miami, 1993. pp. 181-186.
Chardack et al., "Experimental Studies on Synthetic Substitutes for Skin and Their Use in the Treatment of Burns," vol. 155, No. 1 (128-136), 1961.
Chariker, M.E., et al, "Effective Management of Incisional and Cutaneous Fistulae with Closed Suction Wound Drainage," Contemporary Surgery. Jun. 1989, pp. 59-63, vol. 34.
Dilmaghani et al., "A Method for Closed Irrigation and Suction Therapy in Deep Wound Infections," Journal of Bone and Joint Surgery, 1969, vol. 51-A, No. 2, pp. 323-342.
Edlich, R.F., et al.: "Evaluation of a New, Improved Surgical Drainage System," The American Journal of Surgery, vol. 149, pp. 295-298, Feb. 1985.
Fleischmann, "Vacuum Sealing for Treatment of Problematical Wounds", University Surgical Clinic and Polyclinic—Accident Surgery Department, WundForum Spezial-IHW, 1994.
Fleischmann, W. Wund Forum Spezial, "Vakuumversiegelung zur Behandlung von Problemwunden" (with English translation: Vacuum Sealing for Treatment of Problematical Wounds), IHW '94, 6 pages.
Garcia-Rinaldi, R., et al., Improving the Efficiency of Wound Drainage Catheters, Amer. Journ. of Surg., Sep. 1975, 130, 372-373.
Gorica Zivadinovic, et al., "Vacuum Therapy in the Treatment of Peripheral Blood Vessels," Conference Papers of the 5th Timok Medical Days, Majdanpek, 1986 (161-164).
Health Technology, Literature R., "Vacuum Assisted Closure Therapy for Wound Care", Health Technology Literature Review (Dec. 2004), 3-59.
Hough, M.C. et al., "The Plastics Compendium—vol. 2, Comparative Materials Selection Data", Rapra Technology Ltd.,1998, in 4 pages.
Jeter, Katherine F., et al., "Managing Draining Wounds and Fistulae: New and Established Methods", Chronic Wound Care, 1990, pp. 240-246.
Kendall ULTEC Hydrocolloid Dressing (4"×4"), product ordering page, web page downloaded Jul. 13, 2014.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.

Kostiuchenok, et al., "The Vacuum Effect in the Surgical Treatment of Purulent Wounds," Russian Journal: Vestnik Khirurgii, 1986, Sep. (18-21).
McLaughlan, James, Sterile Microenvironment for Postoperative Wound Care, The Lancet, pp. 503-504, Sep. 2, 1978.
Meyer, Md., et al., "In Surgery, Medicine and the Specialties a Manual of its Practical Application", Bier's Hyperemic Treatment, Second Revised Edition, W.B. Saunders Company, 1909.
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
Mulder, GD, et al., "Clinicians' Pocket Guide to Chronic Wound Repair," Wound Healing Publications Second Edition, 1991.
Notice of Opposition—Statement of Facts and Evidence re EP 2 437 802, dated Jan. 23, 2017, in 164 pages.
Pentair Pool Products, 2000 Series Stainless Steel D. E. Filters (2006).
Protz, Kerstin: "Modern Wundauflagen unterstutzen Heilungsprozess", Wundversorgung: Indikation and Anwendung, Geriatrie Journal 4/05, pp. 3333-3339.
Renasys EZ System for Negative Wound Therapy, Smith & Nephew announcement, dated Feb. 24, 2009, in 3 pages.
Ryosuke Fujimoro, MD., et al., "Sponge Fixation Method for Treatment of Early Scars," From the Department of Dermatology in the Faculty Medicine, Kyoto University, vol. 42, No. 4, Oct. 1968 (322-326).
Sames, C.P., Sealing of Wounds with Vacuum Drainage, Br. Med. Journ., Nov. 5, 1977, p. 1223, Correspondence.
Sandén, Göran Md., et al., "Staphylococcal Wound Infection in the Pig: Part II. Inoculation, Quantification of Bacteria, and Reproducibility," Annals of Plastic Surgery, vol. 23, No. 3, Sep. 1989, (219-223).
Smith, S.R.G., et al.: "Surgical drainage," British Journal of Hospital Medicine, Jun. 1985.
Stewart, Joanne, Ph.D., World Wide Wounds—Next generation of products for wound management—2002 (13 pages).
Stoll, "Energetic Remedies—Cupping: Healing Within a Vacuum," https://www.suite101.com/article.cfm/ energetic)remedies/74531, Apr. 13, 2005.
Svedman, "A Dressing Allowing Continuous Treatment of a Biosurface," IRCS Medical Science: Biomedical Technology; Clinical Medicine; Surgery and Transplantation, 7, 221 (1979).
Svedman, "A Dressing System Providing Fluid Supply and Suction Drainage Used for Continuous or Intermittent Irrigation," Annals of Plastic Surgery, vol. 17, No. 2, Aug. 1986 (125-133).
Svedman, P., "Irrigation Treatment of Leg Ulcers," The Lancet, Sep. 3, 1983 (532-534).
Svedman, et al., "Staphylococcal Wound Infection in the Pig: Part I. Course," Annals of Plastic Surgery, vol. 23, No. 3, Sep. 1989 (212-218).
Teder et al., "Continuous Wound Irrigation in the Pig," Journal of Investigative Surgery, 1990, vol. 3, pp. 399-407.
Tribble, David E. M.D., An Improved Sump Drain-Irrigation Device of Simple Construction, Archives of Surgery New York, pp. 511-513, 1972 vol. 105.
Usupov, et al., "Active Wound Drainage," Russian Journal: Vestnik Khirugii, 1987, Apr. (42-45).
Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.
Van Way, C.W., "Prevention of suction-induced gastric mucosal damage in dogs," Crital Care Medicine, vol. 15, No. 8, pp. 774-777, 1987.
Wooding-Scott, Margaret, et al., "No Wound is Too Big for Resourceful Nurses," RN Dec. 1988, pp. 22-25 USA.
Worth, M.H., et al.: "The effectiveness of Bacterial Filtration in Vented Wound Drains," Journal of Surgical Research, 17, 405-407, 1979.
Wu, W.S., et al. Vacuum therapy as an intermediate phase in wound closure: a clinical experience, Eur J Past Surg (2000) 23: 174-177.

(56) References Cited

OTHER PUBLICATIONS

Davydov, Y. et al., "Bacteriological and Cytological Assessment of Vacuum Therapy of Purulent Wounds", Vestnik Khirurgii, 1988, Oct. (48-52).
Davydov, Y. et al., "Concepts for Clinical Biological Management of the Wound Process in the Treatment of Purulent Wounds Using Vacuum Therapy," Vestnik Khirugii, Feb. 1991, 132-135).
Davydov, Y. et al., "Vacuum Therapy in the Treatment of Purulent Lactation Mastitis," Russian Journal: Vesnik Khirurgii, 1986, Sep. (66-70).
Davydov, Y. et al., "Vacuum Therapy in treatment of Acute Purulent Diseases of Soft Tissues and Purulent Wounds," Vestnik Khirurgii, (Surgeon's Herald), Medicine Publishers, 1986.

SYSTEM FOR PROVIDING CONTINUAL DRAINAGE IN NEGATIVE PRESSURE WOUND THERAPY

BACKGROUND

1. Technical Field

The present disclosure relates generally to treating a wound with negative or reduced pressure. In particular, the disclosure relates to a system for providing continual drainage of fluids from a wound site to a collection canister.

2. Background of Related Art

Various techniques to promote healing of a wound involve providing suction to the wound. For example, a vacuum source may serve to carry wound exudates away from the wound, which may otherwise harbor bacteria that inhibit the body's natural healing process. One particular technique for promoting the body's natural healing process may be described as negative pressure wound therapy (NPWT). This technique involves the application of a reduced pressure, e.g. sub-atmospheric, to a localized reservoir over a wound. Sub-atmospheric pressure has been found to assist in closing the wound by promoting blood flow to the area, thereby stimulating the formation of granulation tissue and the migration of healthy tissue over the wound. This technique has proven effective for chronic or non-healing wounds, but has also been used for other purposes such as post-operative wound care.

The general NPWT protocol provides for covering the wound with a flexible cover layer such as a polymeric film, for example, to establish a vacuum reservoir over the wound where a reduced pressure may be applied by individual or cyclic evacuation procedures. To allow the reduced pressure to be maintained over time, the cover layer may include an adhesive periphery that forms a substantially fluid tight seal with the healthy skin surrounding the wound.

Although some procedures may employ a micro-pump contained within the vacuum reservoir, most NPWT treatments apply a reduced pressure using an external vacuum source. Fluid communication must therefore be established between the reservoir and the vacuum source. To this end, a fluid port is coupled to the cover layer to provide an interface for an exudate conduit extending from the external vacuum source. Fluid being drained from the reservoir through the exudate conduit tends to stagnate with slow fluid buildup. This stagnation results in interrupted and/or incomplete fluid drainage. Accordingly, it would be beneficial to have a negative pressure wound therapy system that included a controlled or fixed "leak" to provide for continuous and/or complete fluid drainage.

SUMMARY

A system for subatmospheric pressure therapy in connection with healing a wound is provided. The system includes a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system further includes an exudate conduit in fluid communication with the wound dressing and the collection canister for collecting exudate removed from the reservoir and deposited in the collection canister under influence of the vacuum source and a vent conduit in fluid communication with the collection canister and the wound dressing for introducing air into the reservoir to facilitate flow of exudate through the exudate conduit.

The vent conduit may define an internal dimension less than a corresponding internal dimension of the exudate conduit. The exudate conduit and the vent conduit may include independent tube segments, or instead may include integral tube segments. A filter may be in fluid communication with the vent conduit. The filter includes a hydrophobic material. The filter may instead or additionally include a bacterial filter.

Also provided is a system for subatmospheric pressure therapy in connection with healing a wound including a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system further includes an exudate conduit in fluid communication with the wound dressing and the collection canister for collecting exudate removed from the reservoir and deposited in the collection canister under influence of the vacuum source and a vent mounted to the wound dressing, the vent being selectively movable between a closed position and an open position, the vent permitting ingress of air within the reservoir when in the open position.

The vent may include a flap mounted to the wound dressing cover, the flap being movable between the closed position and the open position. The flap may be releasably securable in the closed position with an adhesive. A filter membrane may be mounted adjacent the flap. The filter membrane may include a hydrophobic material. The filter membrane may instead or additionally include a bacterial filter.

Additionally, provided is a system for subatmospheric pressure therapy in connection with healing a wound including a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system further includes an exudate conduit in fluid communication with the wound dressing and the collection canister for collecting exudate removed from the reservoir and deposited in the collection canister under influence of the vacuum source and a filtered air vent mounted to the wound dressing cover, the filtered air vent adapted to permit ingress of air within the reservoir to facilitate flow of exudate through the exudate conduit.

Additionally, provided is a system for subatmospheric pressure therapy in connection with healing a wound including a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system also includes a wound port operatively connected to the wound dressing in fluid communication with the reservoir. The wound port includes a vacuum port and at least one tube piercing through the wound port into the reservoir, the tube being operable to allow ambient air into the reservoir. The system further includes an exudate conduit in fluid communication with the wound port and the collection canister for collecting exudate removed from the reservoir and deposited in the collection canister under influence of the vacuum.

Additionally, provided is a system for subatmospheric pressure therapy in connection with healing a wound including a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system also includes a wound port operatively connected to the wound dressing in fluid communication with the reservoir. The wound port includes a vacuum port and a plurality of holes arranged circumferentially around the wound port, the plurality of holes being operable to allow ambient air into the reservoir. The system further includes an exudate conduit in fluid communication with the wound port and the collection canister for collecting exudate removed from the reservoir and deposited in the collection canister under influence of the vacuum.

Additionally, provided is a system for subatmospheric pressure therapy in connection with healing a wound including a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system also includes a wound port operatively connected to the wound dressing in fluid communication with the reservoir. The wound port includes a vacuum port and an orifice being operable to allow ambient air into the reservoir. The system further includes an exudate conduit in fluid communication with the wound port and the collection canister for collecting exudate removed from the reservoir and deposited in the collection canister under influence of the vacuum.

Additionally, provided is a system for subatmospheric pressure therapy in connection with healing a wound including a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system also includes a wound port operatively connected to the wound dressing in fluid communication with the reservoir. The system further includes an exudate conduit in fluid communication with the wound port and the collection canister for collecting exudate removed from the reservoir and deposited in the collection canister under influence of the vacuum. The exudate conduit has a first conduit for providing a pathway for the exudate between the reservoir and the collection canister and a second conduit in fluid communication with ambient atmosphere and the wound dressing for introducing air into the reservoir to facilitate flow of exudate through the exudate conduit.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF EMBODIMENTS

Figure 1:
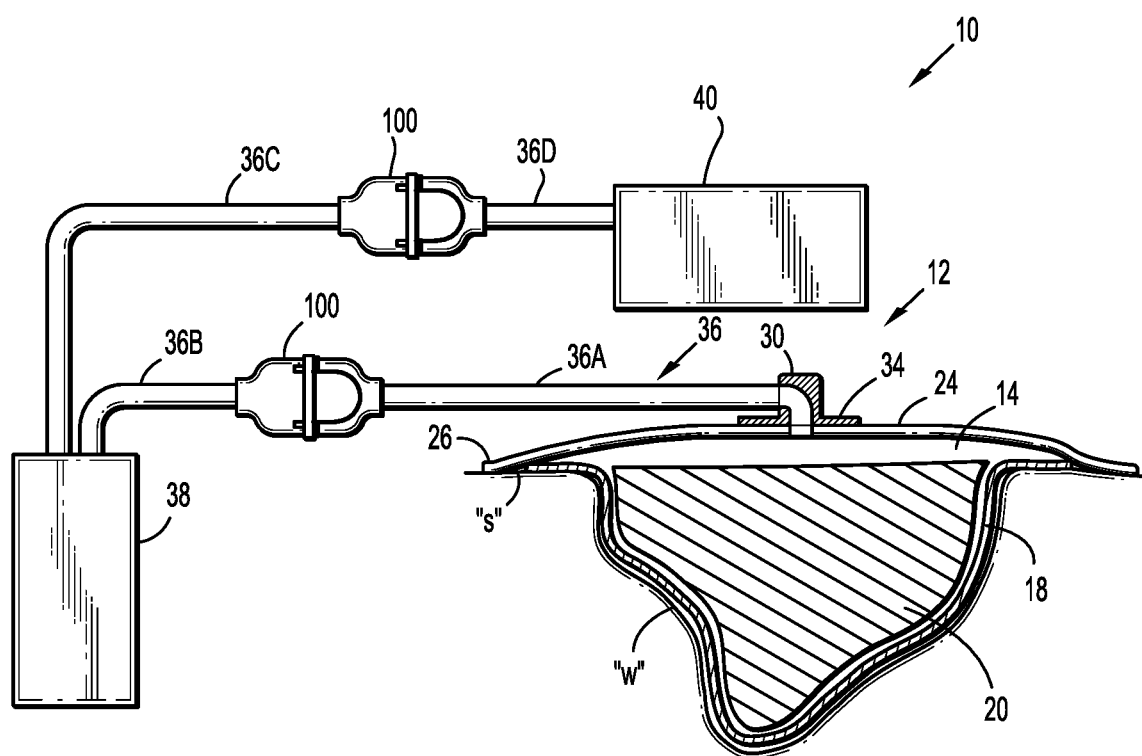
FIG. 1 depicts an embodiment of a NPWT system in accordance with the present disclosure.

Various embodiments of the present disclosure provide negative pressure wound therapy systems (or apparatus) including a collection canister having a chamber to collect wound fluids. Embodiments of the presently disclosed negative pressure wound therapy systems are generally suitable for use in applying negative pressure to a wound to facilitate healing of the wound in accordance with various treatment modalities. Embodiments of the presently disclosed negative pressure wound therapy systems are entirely portable and may be worn or carried by the user such that the user may be completely ambulatory during the therapy period. Embodiments of the presently disclosed negative pressure wound therapy apparatus and components thereof may be entirely reusable or may be entirely disposable after a predetermined period of use or may be individually disposable whereby some of the components are reused for a subsequent therapy application.

Hereinafter, embodiments of the presently disclosed negative pressure wound therapy systems and embodiments of the presently disclosed sensors for use in negative pressure wound therapy systems will be described with reference to the accompanying drawings. Like reference numerals may refer to similar or identical elements throughout the description of the figures. As used herein, "wound exudate", or, simply, "exudate", generally refers to any fluid output from a wound, e.g., blood, serum, and/or pus, etc. As used herein, "fluid" generally refers to a liquid, a gas or both.

Referring to FIG. 1, a NPWT apparatus according to an embodiment of the present disclosure is depicted generally as 10 for use on a wound bed "w" surrounded by healthy skin "s". Negative pressure wound therapy apparatus 10 includes a wound dressing 12 positioned relative to the wound bed "w" to define a vacuum chamber 14 about the wound bed "w" to maintain negative pressure at the wound area. Wound dressing 12 includes a contact layer 18, a wound filler 20 and a wound cover 24.

Contact layer 18 is intended for placement within the wound bed "w" and may be relatively non-supportive or flexible to substantially conform to the topography of the wound bed "w". A variety of materials may be used for the contact layer 18. Contact layer 18 selection may depend on various factors such as the patient's condition, the condition of the periwound skin, the amount of exudate and/or the condition of the wound bed "w". Contact layer 18 may be formed from perforated film material. The porous characteristic of the contact layer 18 permits exudate to pass from the wound bed "w" through the contact layer 18. Passage of wound exudate through the contact layer 18 may be substantially unidirectional such that exudate does not tend to flow back into the wound bed "w". Unidirectional flow may be encouraged by directional apertures, e.g., apertures positioned at peaks of undulations or cone-shaped formations protruding from the contact layer 18. Unidirectional flow may also be encouraged by laminating the contact layer 18 with materials having absorption properties differing from those of the contact layer 18, or by selection of materials that promote directional flow. A non-adherent material may be selected for forming the contact layer 18 such that the contact layer 18 does not tend to cling to the wound bed "w" or surrounding tissue when it is removed. One example of a material that may be suitable for use as a contact layer 18 is commercially available under the trademark XEROFLOW® offered by Tyco Healthcare Group LP (d/b/a Covidien). Another example of a material that may be suitable for use as the contact layer 18 is the commercially available CURITY® non-adherent dressing offered by Tyco Healthcare Group LP (d/b/a Covidien).

Wound filler 20 is positioned in the wound bed "w" over the contact layer 18 and is intended to transfer wound exudate. Wound filler 20 is conformable to assume the shape of any wound bed "w" and may be packed up to any level, e.g., up to the level of healthy skin "s" or to overfill the wound such that wound filler 20 protrudes over healthy skin "s". Wound filler 20 may be treated with agents such as polyhexamethylene biguanide (PHMB) to decrease the incidence of infection and/or other medicaments to promote wound healing. A variety of materials may be used for the wound filler 20. An example of a material that may be suitable for use as the wound filler 20 is the antimicrobial dressing commercially available under the trademark KERLIX™ AMD™ offered by Tyco Healthcare Group LP (d/b/a Covidien).

Cover layer 24 may be formed of a flexible membrane, e.g., a polymeric or elastomeric film, which may include a biocompatible adhesive on at least a portion of the cover layer 24, e.g., at the periphery 26 of the cover layer 24. Alternately, the cover layer 24 may be a substantially rigid member. Cover layer 24 may be positioned over the wound bed "w" such that a substantially continuous band of a biocompatible adhesive at the periphery 26 of the cover layer 24 forms a substantially fluid-tight seal with the surrounding skin "s". An example of a material that may be suitable for use as the cover layer 24 is commercially available under the trademark CURAFORM ISLAND® offered by Tyco Healthcare Group LP (d/b/a Covidien).

Cover layer 24 may act as both a microbial barrier and a fluid barrier to prevent contaminants from entering the wound bed "w" and to help maintain the integrity thereof.

In one embodiment, the cover layer 24 is formed from a moisture vapor permeable membrane, e.g., to promote the exchange of oxygen and moisture between the wound bed "w" and the atmosphere. An example of a membrane that may provide a suitable moisture vapor transmission rate (MVTR) is a transparent membrane commercially available under the trade name POLYSKIN® II offered by Tyco Healthcare Group LP (d/b/a Covidien). A transparent membrane may help to permit a visual assessment of wound conditions to be made without requiring removal of the cover layer 24.

Wound dressing 12 may include a vacuum port 30 having a flange 34 to facilitate connection of the vacuum chamber 14 to a vacuum system. Vacuum port 30 may be configured as a rigid or flexible, low-profile component and may be adapted to receive a conduit 36 in a releasable and fluid-tight manner. An adhesive on at least a portion of the underside of the flange 34 may be used to provide a mechanism for affixing the vacuum port 30 to the cover layer 24. The relative positions, size and/or shape of the vacuum port 30 and the flange 34 may be varied from an embodiment depicted in FIG. 1. For example, the flange 34 may be positioned within the vacuum chamber 14 such that an adhesive on at least a portion of an upper side surface of the flange 34 affixes the vacuum port 30 to the cover layer 24. A hollow interior portion of the vacuum port 30 provides fluid communication between the conduit 36 and the vacuum chamber 14. Conduit 36 extends from the vacuum port 30 to provide fluid communication between the vacuum chamber 14 and the vacuum source 40. Alternately, the vacuum port 30 may not be included in the dressing 12 if other provisions are made for providing fluid communication with the conduit 36.

Any suitable conduit may be used for the conduit 36, including conduit fabricated from flexible elastomeric or polymeric materials. In the negative pressure wound therapy apparatus 10 illustrated in FIG. 1, the conduit 36 includes a first conduit section 36A, a second conduit section 36B, a third conduit section 36C and a fourth conduit section 36D. The first conduit section 36A extends from the vacuum port 30 and is coupled via a fluid line coupling 100 to the second conduit section 36B, which extends to the collection canister 38. The third conduit section 36C extends from the collection canister 38 and is coupled via another fluid line coupling 100 to the fourth conduit section 36D, which extends to the vacuum source 40. The shape, size and/or number of conduit sections of the conduit 36 may be varied from the first, second, third and fourth conduit sections 36A, 36B, 36C and 36D depicted in FIG. 1.

The first, second, third and fourth conduit sections 36A, 36B, 36C and 36D of the conduit 36 may be connected to components of the apparatus 10 by conventional air-tight means, such as, for example, friction fit, bayonet coupling, or barbed connectors. The connections may be made permanent. Alternately, a quick-disconnect or other releasable connection means may be used to provide some adjustment flexibility to the apparatus 10.

Collection canister 38 may be formed of any type of container that is suitable for containing wound fluids. For example, a semi-rigid plastic bottle may be used for the collection canister 38. A flexible polymeric pouch or other hollow container body may be used for the collection canister 38. Collection canister 38 may contain an absorbent material to consolidate or contain the wound fluids or debris. For example, super absorbent polymers (SAP), silica gel, sodium polyacrylate, potassium polyacrylamide or related compounds may be provided within collection canister 38. At least a portion of canister 38 may be transparent or semi-transparent, e.g., to permit a visual assessment of the wound exudate to assist in evaluating the color, quality and/or quantity of exudate. A transparent or semi-transparent portion of the collection canister 38 may permit a visual assessment to assist in determining the remaining capacity or open volume of the canister and/or may assist in determining whether to replace the collection canister 38.

The collection canister 38 is in fluid communication with the wound dressing 12 via the first and second conduit sections 36A, 36B. The third and fourth conduit sections 36C, 36D connect the collection canister 38 to the vacuum source 40 that generates or otherwise provides a negative pressure to the collection canister 38. Vacuum source 40 may include a peristaltic pump, a diaphragmatic pump or other suitable mechanism. Vacuum source 40 may be a miniature pump or micropump that may be biocompatible and adapted to maintain or draw adequate and therapeutic vacuum levels. The vacuum level of subatmospheric pressure achieved may be in the range of about 20 mmHg to about 500 mmHg. In embodiments, the vacuum level may be about 75 mmHg to about 125 mmHg, or about 40 mmHg to about 80 mmHg One example of a peristaltic pump that may be used as the vacuum source 40 is the commercially available Kangaroo PET Eternal Feeding Pump offered by Tyco Healthcare Group LP (d/b/a Covidien). Vacuum source 40 may be actuated by an actuator (not shown) which may be any means known by those skilled in the art, including, for example, alternating current (AC) motors, direct current (DC) motors, voice coil actuators, solenoids, and the like. The actuator may be incorporated within the vacuum source 40.

In embodiments, the negative pressure wound therapy apparatus 10 includes one or more fluid line couplings 100 that allow for selectable coupling and decoupling of conduit sections. For example, a fluid line coupling 100 may be used to maintain fluid communication between the first and second conduit sections 36A, 36B when engaged, and may interrupt fluid flow between the first and second conduit sections 36A, 36B when disengaged. Thus, fluid line coupling 100 may facilitate the connection, disconnection or maintenance of components of the negative pressure wound therapy apparatus 10, including the replacement of the collection canister 38. Additional or alternate placement of one or more fluid line couplings 100 at any location in line with the conduit 36 may facilitate other procedures. For example, the placement of a fluid line coupling 100 between the third and fourth conduit sections 36C, 36D, as depicted in FIG. 1, may facilitate servicing of the vacuum source 40.

Figure 2:
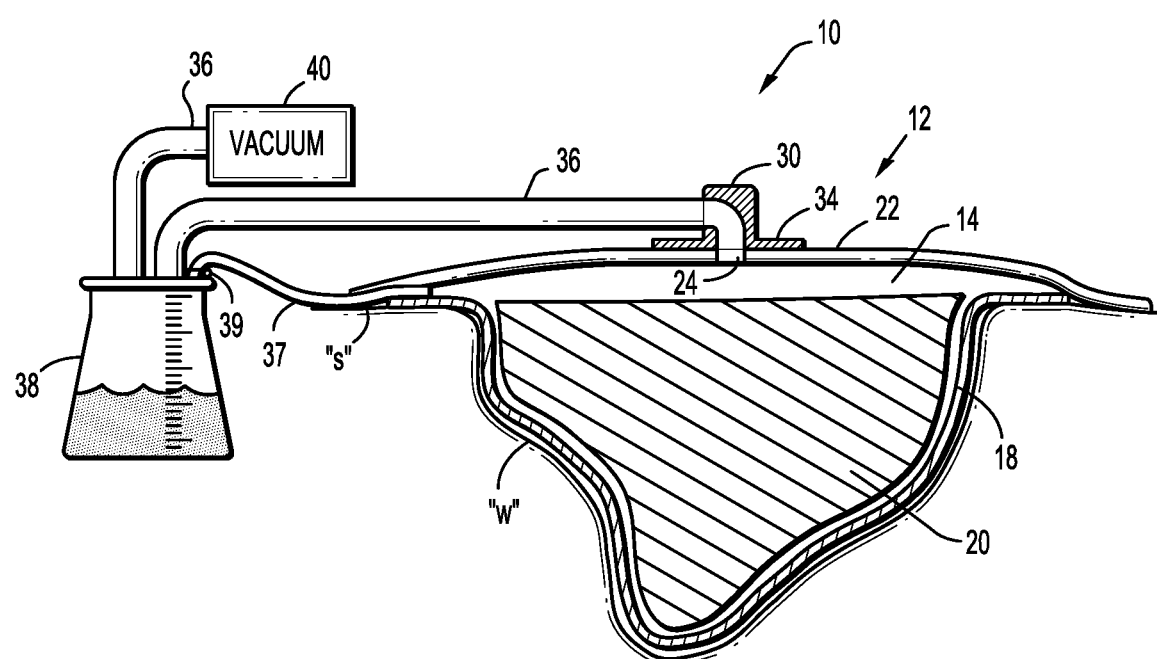
FIG. 2 depicts an embodiment of an NPWT treatment apparatus including a vent conduit.

Referring to FIG. 2, an NPWT apparatus similar to the NPWT apparatus of FIG. 1 is depicted generally as 10 for use on a wound "w" surrounded by healthy skin "s." The NPWT apparatus 10 of FIG. 2 includes a vent conduit 37 that extends from between contact layer 18 and cover layer 22 of wound dressing 12 to collection canister 38. Vent conduit 37 may be integral formed with wound dressing 12. Alternatively, vent conduit 37 may be inserted between contact layer 18 and cover layer 22 by a clinician during application of the wound dressing 12, or may have been previously inserted therebetween prior to application. Vent conduit 37 may be releasably connected to the collection canister 38 by conventional air-tight means such as friction fit, bayonet coupling, or barbed connectors.

Vent conduit 37 is configured to provide a low flow of air from the reservoir 14 to the collection canister 38. Vent conduit 37 includes a smaller diameter than exudate conduit 36 and may be formed of any suitable conduit including those fabricated from flexible elastomeric or polymeric materials. An air filter 39 positioned along the air flow path filters the air flowing from collection canister 38 to remove any impurities, including bacteria and other infectious material. Filter 39 may include a hydrophobic material to prevent wetting.

In operation, wound dressing 12 is placed adjacent a wound "w" with the vent conduit 37 extending from between the contact layer 18 and the cover layer 22. If the vent conduit 37 is not integral formed with the wound dressing 12, the clinician may be required to position the vent conduit 37 between the layers during application of the wound dressing 12. Vacuum source 50 is then activated to produce a sub-atmospheric pressure in the reservoir 14 of the wound dressing 12. Fluid from the reservoir 14 is drawn through aperture 24 in cover layer 22, into fluid port 30 and along exudate conduit 36 to be deposited in collection canister 40. As fluid and other exudates are drawn through exudate conduit 36, filtered air is received within the reservoir 14 of the wound dressing 12 through the vent conduit 37. The low flow filtered air flowing from the collection canister 38 through the vent conduit 37, in combination with the high flow drainage occurring through exudate conduit 36, creates a sump action between the reservoir 14 and the collection canister 40. This sump action ensures continuous flow through exudate conduit 36, thereby preventing fluid stagnation and its complications. Because of capillary action, fluid from reservoir 14 only flows through the larger diameter exudate conduit 36.

Figure 3A:
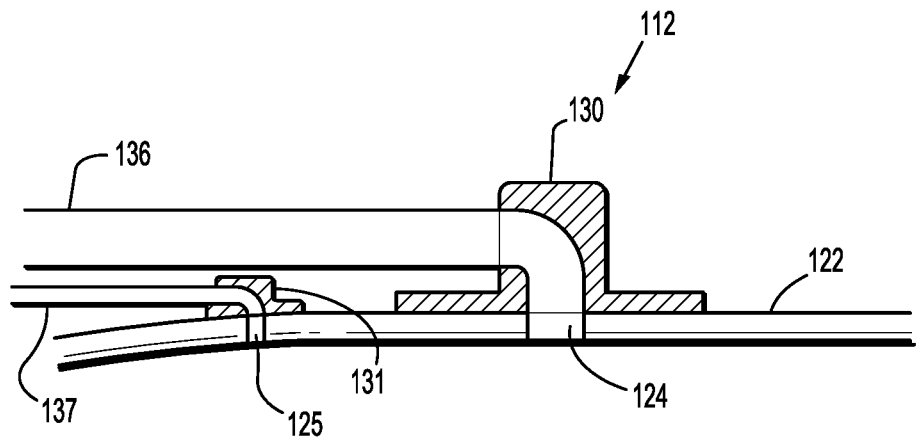
FIG. 3A is a partial cross sectional view of the conduits of the NPWT treatment apparatus of FIGS. 1 and 2 connected in an alternate configuration.

With reference now to FIG. 3A, in an alternative embodiment of the present disclosure, a wound dressing 112 is substantially similar to wound dressing 12 described hereinabove, and will only be described as relates to the differences therebetween. Wound dressing 112 includes a cover layer 122 having a first or fluid aperture 124 and a second or vent aperture 125. A fluid port 130 is in fluid communication with fluid aperture 124 and is configured for operable engagement with exudate conduit 136. A vent port 131 is in fluid communication with vent aperture 125 and is configured for operable engagement with vent conduit 137. Fluid and vent ports 130, 131 may be affixed to cover layer 122 in any suitable manner. Each of fluid and vent port 130, 131 are in fluid communication with collection canister 38 (FIGS. 1 and 2).

Wound dressing 112 operates in substantially the same manner as wound dressing 12. When connected to collection canister 40 and the vacuum source 50 is activated, the sub-atmospheric pressure produced by the vacuum source 50 creates a suction that draws fluid from the reservoir 114. Vent conduit 137 provides the reservoir 114 with a low flow of filtered air to ensure continuous fluid flow through the exudate conduit 136.

Figure 3B:
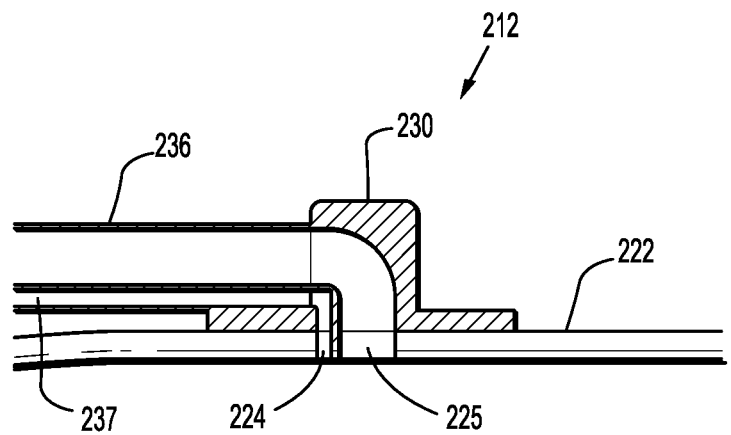
FIG. 3B is a partial cross sectional view of an alternative embodiment of the fluid port of FIGS. 1 and 2.

Turning now to FIG. 3B, in another embodiment, wound dressing 212 is substantially similar to the wound dressings 12, 112 described hereinabove. Wound dressing 212 includes a cover layer 222 having a first and second aperture 224, 225. Positioned adjacent first and second apertures 224, 225 is a fluid/vent port 230. Port 230 is configured to fluidly communicate first aperture 224 of wound dressing 212 with collection canister 38 (FIGS. 1 and 2) via exudate conduit 236. Port 230 is further configured to fluidly communicate second aperture 225 of wound dressing 212 with collection canister 40 via vent conduit 237. As discussed above, the difference in size between exudate conduit 236 and vent conduit 237 results in capillary action that causes fluid to flow only through the larger exudate conduit 36.

Figure 4:
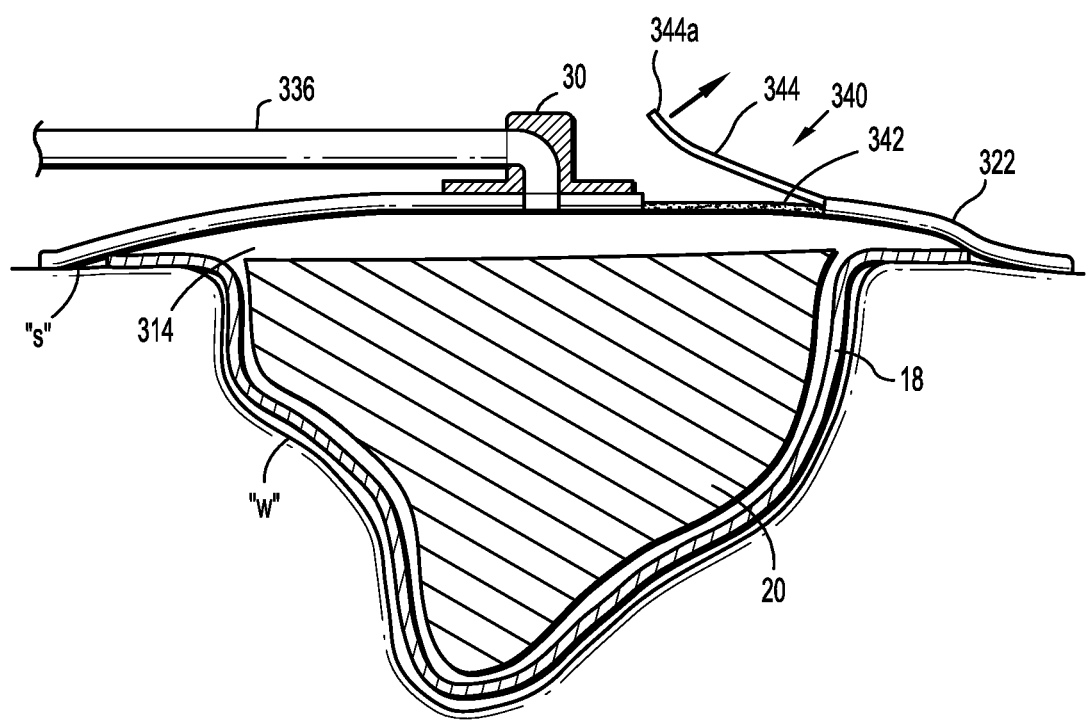
FIG. 4 is a cross sectional view of an alternative embodiment of the wound dressing in accordance with the present disclosure.

With reference now to FIG. 4, in yet another embodiment, a wound dressing 312 similar to those described above including a vent assembly 340 formed in a cover layer 322. Vent assembly 340 includes a filter member 342 and a flap or cover member 344. Filter member 342 may be integrally formed with, or otherwise affixed to, the cover layer 322. In one embodiment, filter member 342 is secured to the cover layer 322 with an adhesive. Filter member 342 is configured to provide reservoir 314 of wound dressing 312 with filtered air. To prevent wetting, the filter member 342 may be hydrophobic. Filter member 342 may be sized depending on the desired flow therethrough. A larger filter member 342 would provide a greater amount of airflow; however, if the filter member 342 is too large, it may reduce the effectiveness of the NWPT.

Flap 344 may be integrally formed with cover layer 322. Alternatively, flap 344 may be releasably secured over filter member 342. Flap 344 may be attached to or separable from cover member 322. Flap 344 may be configured to selectively partially or completely uncover filter member 342. In this manner, a clinician may affect the flow of air into the reservoir 314. Although shown including flap 344, it is envisioned that wound dressing 312 may be provided with filter member 342 exposed.

In use, wound dressing 312 is applied to a wound "w" in a conventional manner. Activation of the vacuum source 40 (FIGS. 1 and 2) initiates drainage from reservoir 314 of wound dressing 312. At any time prior to or during the drainage process, flap 344 may be partially or complete pulled back to expose filter member 342. As described above, the more of filter member 342 that is exposed, the greater the possible airflow into reservoir 14. The airflow provided to reservoir 14 through filter member 342 acts in a manner similar to the sump action described above. In this manner, vent assembly 340 permits continuous fluid flow through exudate conduit 336, thereby preventing fluid stagnation and its complications.

Figure 5A:
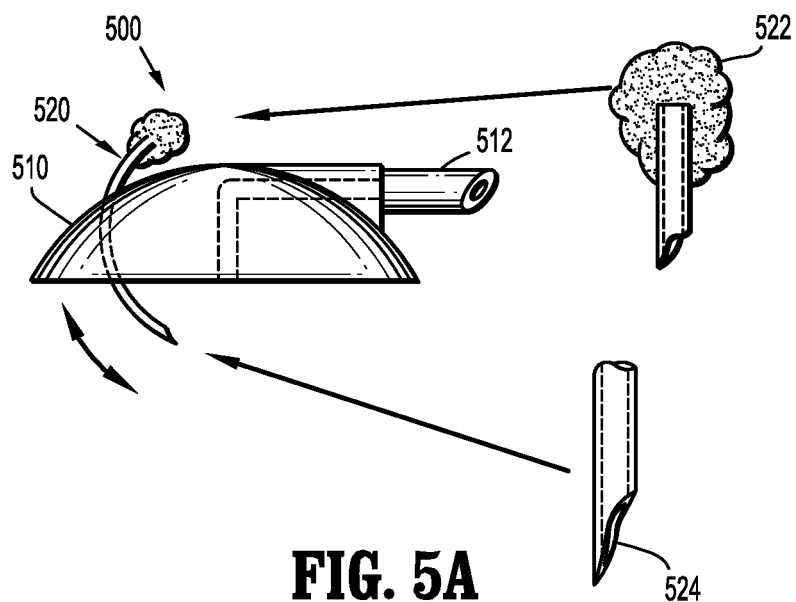
FIGS. 5A and 5B depict alternative embodiments of the wound dressing in accordance with the present disclosure.
Figure 5B:
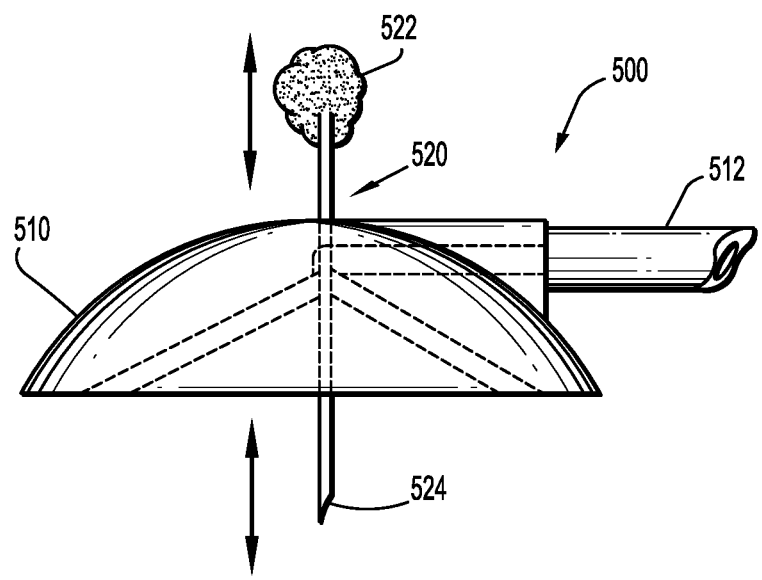

With reference to FIGS. 5A and 5B, in yet another embodiment, a wound port 500 is shown. Wound port 500 is suitable for use with the above described wound dressings. Wound port 500 has a plastic cover 510 which includes a vacuum port 512. In addition to the vacuum port 512, the plastic cover 510 has tube 520. Tube 520 may be made of a small-bore stainless steel or rigid plastic. Tube 520 is used to provide a controlled or fixed leak by admitting air into the wound dressing. Tube 520 can be arranged to allow the insertion of tube 520 into the wound port 500 so that depth adjustment and placement within the wound packing material is possible as indicated by the arrows in FIGS. 5A and 5B. As such, air can be injected into the wound packing material to direct movement of excess exudate toward the vacuum port and out of the wound. Tube 520 may have a valve (not shown) to adjust the flow rate of air into the wound bed. The valve may be a small needle valve that can be attached to the tube 520 to allow for infinite adjustment of air flow into the wound dressing.

The end of tube 520 that may be exposed to ambient atmosphere or to a source of air may include a filter 522. Filter 522 may be a q-tip like air filter to prevent clogging of the tube and also prevent dirt and other contaminants from entering the wound site. Alternatively, filter 522 may include a charcoal filter to prevent odor, a hydrophobic filter, or any sintered or porous material. The tip of tube 520 that is inserted into the wound packing material may be equipped with a puncturing tip 524 to allow for easier insertion into the wound packing material.

Figure 6A:
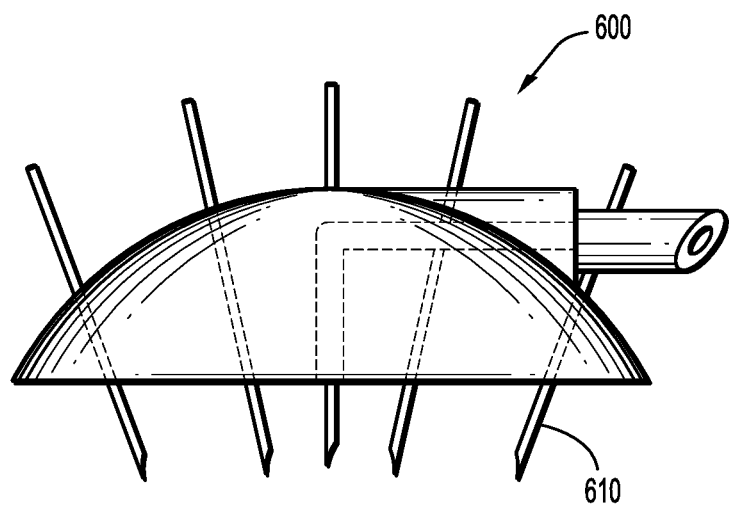
FIGS. 6A and 6B depict alternative embodiments of the wound dressing in accordance with the present disclosure.
Figure 6B:
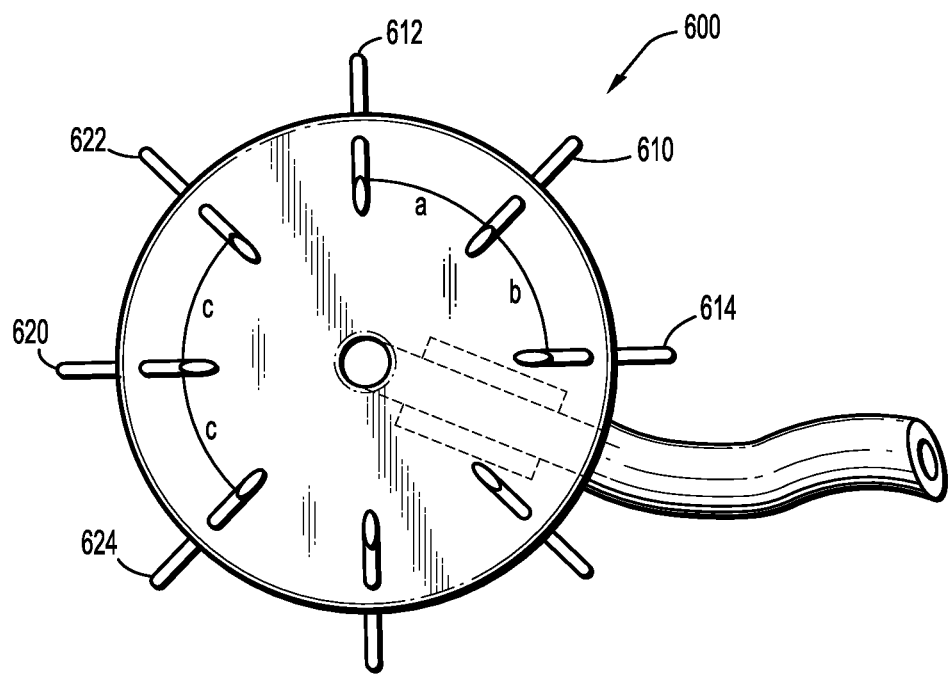

With reference to FIGS. 6A and 6B, in yet another embodiment, a wound port 600 is shown. As shown in FIG. 6A, wound port 600 has tube 610 in separate locations around a circumference of the wound port 600. Each tube may include a punctured tip or a filter as described above. As shown in FIG. 6B, the distance "a" between tube 610 and tube 612 may be one distance and the distance "b" between tube 610 and 614 may be a distance different the distance "a". On the other hand, the difference between each tube may be similar as in the distance "c" between tube 620 and 622 and tube 620 and 624. Although FIGS. 6A and 6B show a specific number of tubes, any number of tubes may be arranged outside a circumference of the wound port 600.

Figure 7A:
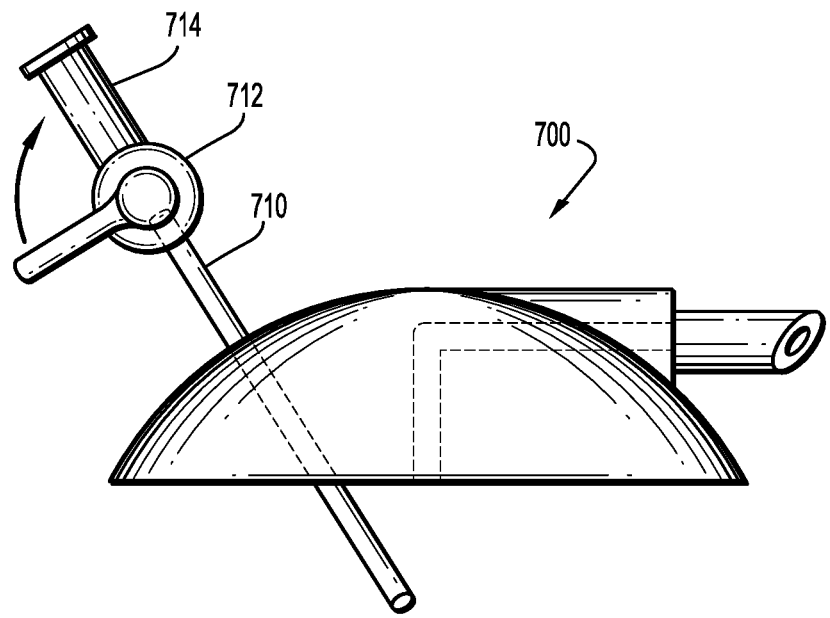
FIGS. 7A and 7B depict alternative embodiments of the wound dressing in accordance with the present disclosure.
Figure 7B:
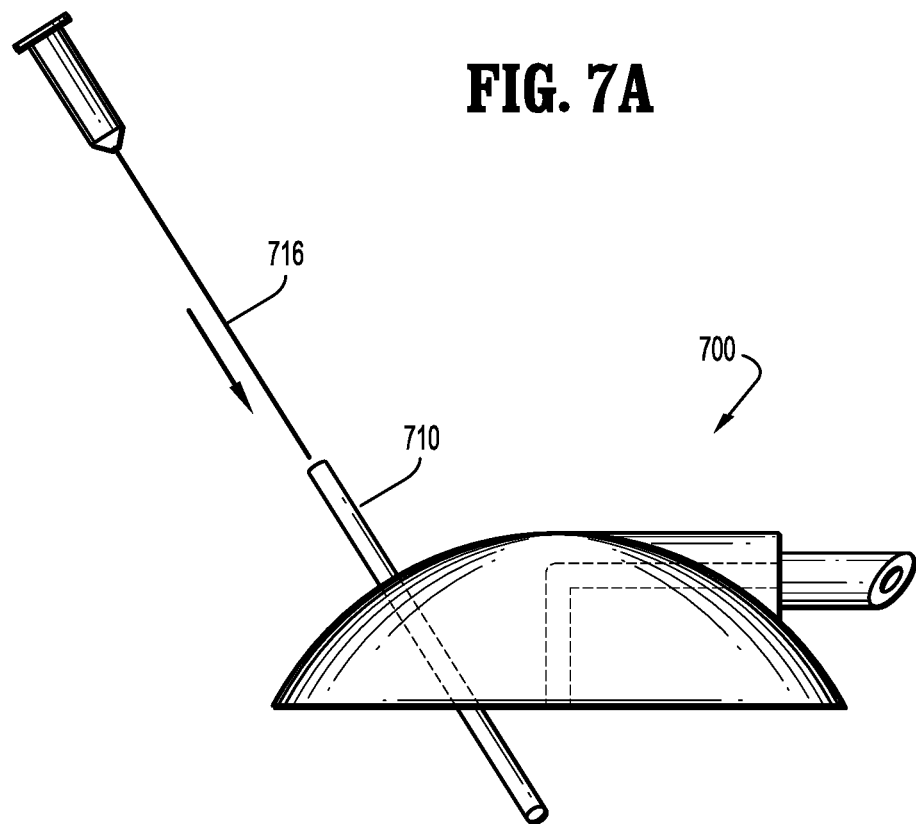

With reference to FIGS. 7A and 7B, in yet another embodiment, a wound port 700 is shown having a tube 710 which is similar to the tubes described above. Tube 710 may be slightly larger in diameter to allow for fluids to enter the wound site. The fluids may include a solution to flush the wound such as saline or it may be an anesthetic to anesthetize the wound area. Tube 710 may be fitted with valve 712 to open and close the pathway into the wound site. Additionally, the end of tube 710 may be fitted with a luer connector 714 to create a fluid tight connection with additional tubing, syringes, or any other conduits. Alternatively, instead of a valve, a plug (not shown) could be used to close the luer connector. With reference to FIG. 7B, a hypodermic needle 716 may be inserted into tube 710. Hypodermic needle 716 could be used to deliver a solution to a specific area of the wound or it could be used to obtain a sample of blood, exudate or tissue from the wound site.

Figure 8A:
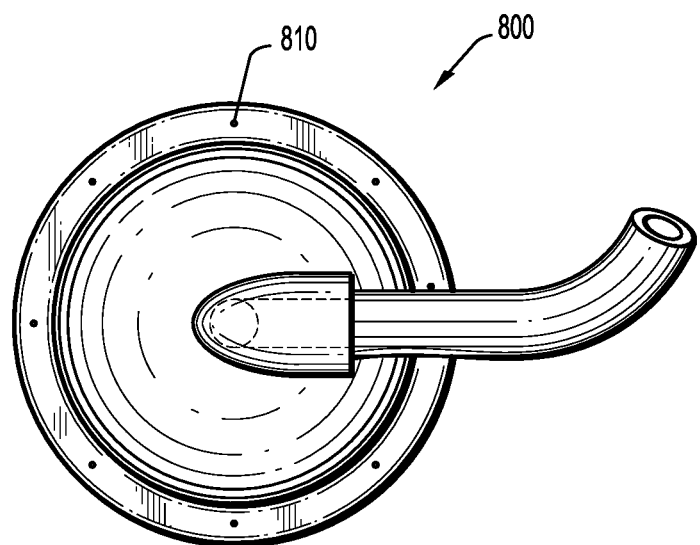
FIGS. 8A and 8B depict alternative embodiments of the wound dressing in accordance with the present disclosure.
Figure 8B:
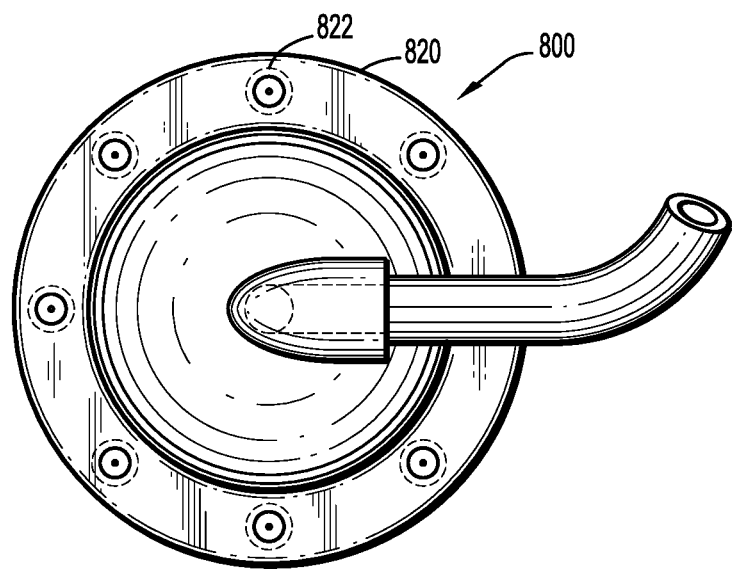

With reference to FIGS. 8A and 8B, in yet another embodiment, a wound port 800 is shown. Instead of using tubes as described above to allow a controlled or fixed leak, a number of small holes arranged in a circumference around the wound port 800 may be provided. The holes may take the form of a simple puncture 810 of a given size as shown in FIG. 8A. Alternatively, the holes 822 may be formed in a plate 820 that is radio frequency (RF) welded to the wound port 800.

Figure 9:
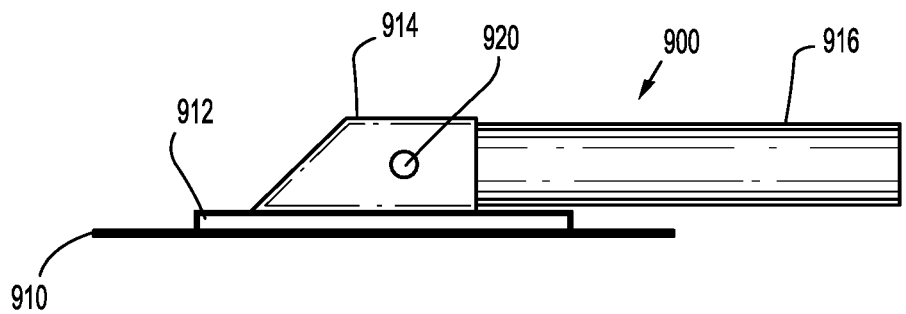
FIG. 9 depicts an alternative embodiment of the wound port in accordance with the present disclosure.

With reference to FIG. 9, in yet another embodiment, a cross section of wound port 900 is shown. Wound port 900 is operatively connected to wound dressing 910 and includes a flange 912. Flange 912 may have a circular or any polygonal shape. A body 914 is connected to the flange 912 which is fluidly connected to conduit 916. Conduit 916 leads directly or indirectly to the collection canister. Body 914 has as small orifice 920 used to provide a controlled leak into the wound site. The diameter of the orifice 920 and the pressure difference between the outside of the wound port 900 and the inside of the wound port 90 create a controllable air leak into the wound port 900 via the orifice. The small orifice 920 can be created in various ways. The orifice 920 can be integral to the port design, such as a molded in feature. It can be created via post molding micro-piercing into the port using a needle or syringe. Alternatively, assembly or insertion of a small tube that allows for communication of air from outside the wound port 900 to inside the wound port 900 can be used to create the orifice 920.

Figure 10A:
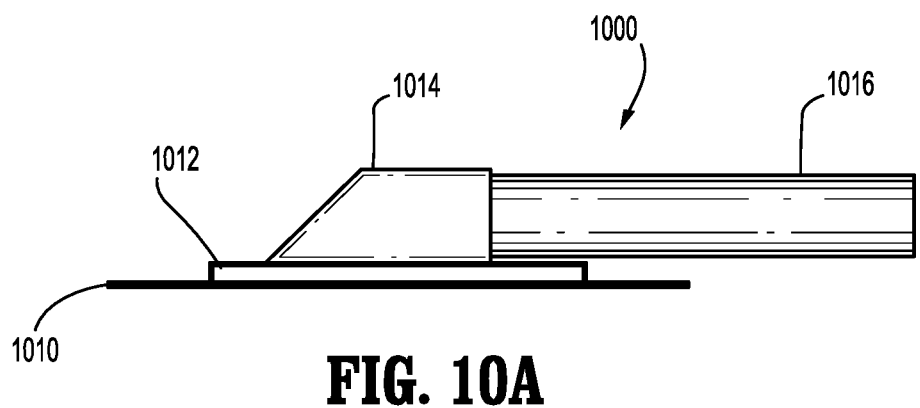
FIGS. 10A and 10B depict alternative embodiments of the wound port in accordance with the present disclosure.
Figure 10B:
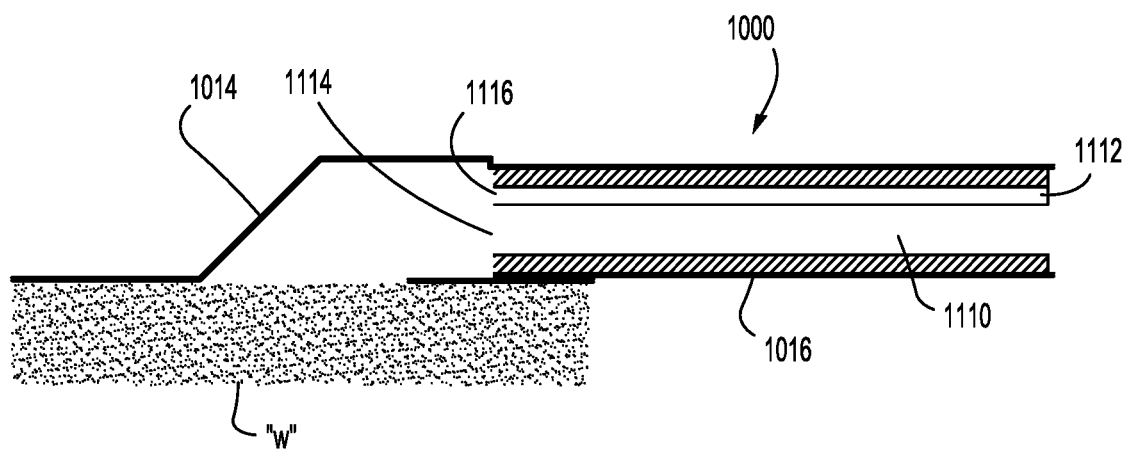

With reference to FIGS. 10A and 10B, in yet another embodiment, a wound port 1000 is shown. Wound port 1000 is operatively connected to wound dressing 1010 and includes a flange 1012. Flange 1012 may have a circular or any polygonal shape. A body 1014 is connected to the flange 1012 which is fluidly connected to conduit 1016. Conduit 1016 leads directly or indirectly to the collection canister. Conduit 1016 includes a main lumen 1110 used to provide a pathway for exudate between the wound "w" and the collection canister. A secondary lumen or vent lumen is provided in conduit 1016 to provide a controlled leak to the wound site. Exudate enters lumen 1110 at area 1114 and air exits lumen 1112 at area 1116. Secondary lumen 1112 is exposed to the ambient environment or to a source of air to provide a controlled leak in the wound port 1000. Although FIG. 10B depicts lumens 1110 and 1112 in a single conduit 1016, lumens 1110 and 1112 can be provided as separate conduits.

Figure 11A:
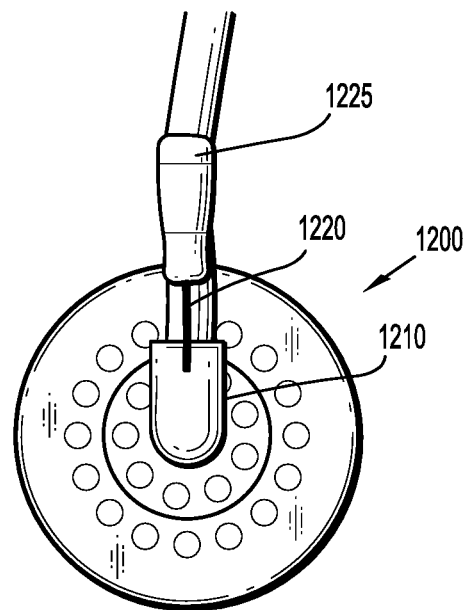
FIGS. 11A-11D depict alternative embodiments of the wound port in accordance with the present disclosure.
Figure 11B:
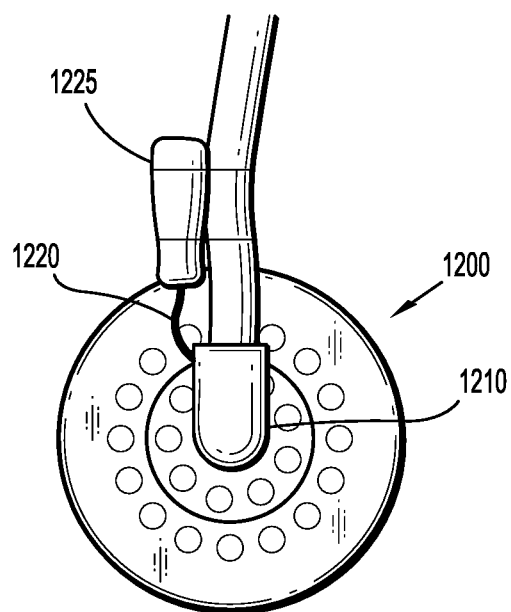
Figure 11C:
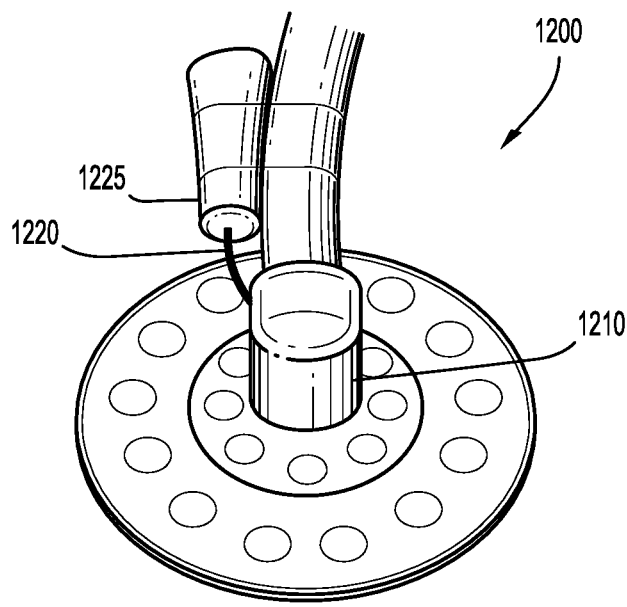
Figure 11D:
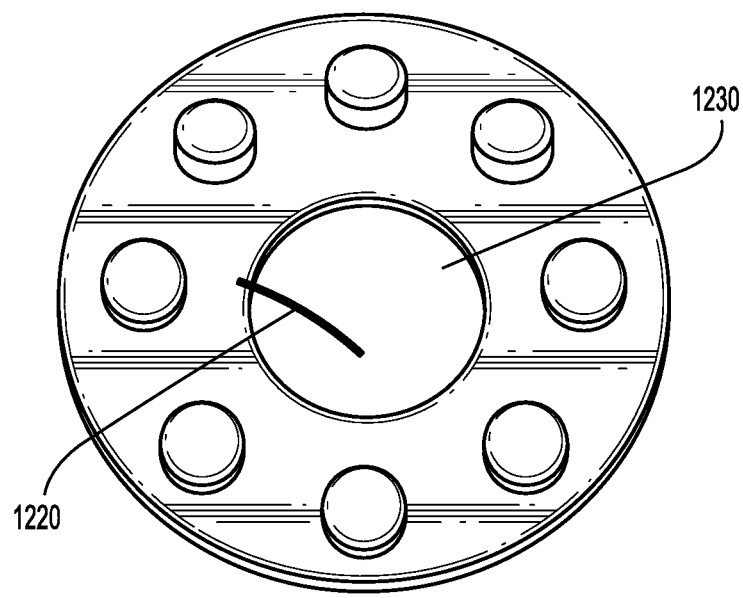

With reference to FIG. 11A, in yet another embodiment, a wound dressing 1200 is shown having a wound port 1210. Wound dressing 1200 and wound port 1210 are similar to wound dressing 12, 112, and 212 and wound port 1210 are similar to wound port 30, 130 and 230 described hereinabove. A vent conduit 1220 may be inserted into the top of wound port 1210 to provide a source of filtered air into the wound dressing 1200 through the vent conduit 1220. Vent conduit 1220 may be a stainless steel needle having a lumen extending through the needle. The end of vent conduit 1220 has filter 1225 to filter the air from the ambient atmosphere. The low flow filtered air flowing from the ambient atmosphere through the vent conduit 1220, in combination with the high flow drainage occurring through an exudate conduit, creates a sump action between the wound and a collection canister. This sump action ensures continuous flow through exudate conduit 36, thereby preventing fluid stagnation and its complications. As discussed above, the difference in size between exudate conduit and vent conduit 1220 results in capillary action that causes fluid to flow only through the larger exudate conduit. FIGS. 11B-11D depict a wound port 1210 similar to the wound port in FIG. 11A. In FIGS. 11B-11D, the vent conduit 1220 is placed on the side of the wound port 1210 rather than the top of the wound port 1210 as shown in FIG. 11A. FIG. 11D depicts the end of vent conduit 1220 being located in the wound port 1210 above an exudate orifice 1230.

Although the foregoing disclosure has been described in some detail by way of illustration and example, for purposes of clarity or understanding, it will be obvious that certain changes and modifications may be practiced within the scope of the appended claims. For example, the individual fluid and vent conduits may be substituted for by a conduit having a dual lumen. To ensure the capillary action, one lumen must be larger than the other; however, the lumens may be coaxial or parallel.

What is claimed is:

1. A negative pressure wound therapy system comprising:
    a wound dressing comprising a cover layer configured to be placed over a wound and form a substantially fluid tight seal around the wound; and
    a port configured to be positioned over and attached to the cover layer in order to be in fluid communication with the wound, the port comprising:
        a wound-facing surface configured to be positioned over the cover layer;
        a central opening configured to be in fluid communication with an elongate conduit; and
        one or more fluid flow paths, wherein at least one fluid flow path of the one or more fluid flow paths extends beyond the wound-facing surface of the port; and
    the elongate conduit configured to fluidically connect the port to a negative pressure source to provide negative pressure to the wound, wherein the elongate conduit is independent of the one or more fluid flow paths.

2. The system according to claim 1, wherein the at least one fluid flow path is configured to extend into the wound when the port is attached to the cover layer.

3. The system according to claim 1, wherein the at least one fluid flow path includes a filter at an end opposite from an end that extends beyond the wound-facing surface of the port.

4. The system according to claim 1, wherein the at least one fluid flow path includes a puncturing tip at an end that extends beyond the wound-facing surface of the port.

5. The system according to claim 1, wherein the at least one fluid flow path comprises a valve operable to control a flow of fluid into the wound.

6. The system according to claim 5, wherein the valve is a needle valve.

7. The system according to claim 1, wherein each of the one or more fluid flow paths extends beyond the wound-facing surface of the port.

8. The system according to claim 7, wherein the port is circular, and wherein the one or more fluid flow paths are placed around an interior circular portion of the port.

9. The system according to claim 1, wherein the wound dressing further comprises a wound packing material configured to be disposed in the wound, and wherein the at least one fluid flow path is configured to extend into the wound packing material when the port is attached to the cover layer.

10. The system according to claim 1, wherein the at least one fluid flow path is configured to introduce atmospheric air under the cover layer.

11. The system according to claim 1, wherein the one or more fluid flow paths comprise tubes.

12. The system according to claim 1, wherein the at least one fluid flow path is configured to introduce fluid under the cover layer.

13. A method of providing negative pressure wound therapy, the method comprising:
    positioning a wound dressing comprising a cover layer over a wound to form a substantially fluid tight seal around the wound;
    positioning over and attaching to the cover layer a wound-facing surface of a port, wherein the port comprises one or more fluid flow paths, and wherein at least one fluid flow path of the one or more fluid flow paths extends beyond the wound-facing surface of the port and includes an end positioned at least partially under the cover layer and in the wound; and
    connecting a negative pressure source to the port via an elongate conduit, wherein the port comprises a central opening in fluid communication with the elongate conduit, and wherein the elongate conduit is independent of the one or more fluid flow paths.

14. The method according to claim 13, wherein each of the one or more fluid flow paths extends beyond the wound-facing surface of the port.

15. The method according to claim 13, further comprising positioning wound packing material in the wound, and wherein the end of the at least one fluid flow path at least partially extends into the wound packing material.

16. The method according to claim 13, further comprising introducing fluid into the wound through the at least one fluid flow path.

17. The method according to claim 16, further comprising introducing atmospheric air through the at least one fluid flow path.

* * * * *